United States Patent [19]

Xanthopoulos

[11] 4,148,316
[45] Apr. 10, 1979

[54] SELF-SEALED HYPODERMIC SYRINGE

[75] Inventor: Piritheos Xanthopoulos, Cupertino, Calif.

[73] Assignee: Stewart-Naumann Laboratories, Inc., Santa Clara, Calif.

[21] Appl. No.: 828,516

[22] Filed: Aug. 29, 1977

[51] Int. Cl.$^2$ ............................................. A61M 5/00
[52] U.S. Cl. .................................. 128/218 S; 128/221
[58] Field of Search ............ 128/218 R, 218 S, 218 P, 128/218 PA, 218 N, 221, 220, 234, 215, 216; 206/365, 571

[56]  References Cited

U.S. PATENT DOCUMENTS

| 3,485,239 | 12/1969 | Vanderbeck | 128/218 S |
| 3,677,245 | 7/1972 | Welch | 128/218 S |
| 3,677,247 | 7/1972 | Brown | 128/221 |
| 3,820,652 | 6/1974 | Thackston | 128/221 X |
| 3,828,775 | 8/1974 | Armel | 128/218 S X |

Primary Examiner—John D. Yasko
Attorney, Agent, or Firm—Flehr, Hohbach, Test, Albritton & Herbert

[57] ABSTRACT

A self-sealed hypodermic syringe uses Louis Pasteur's principle of the "tortuous path" to maintain a sterile condition within a medicament chamber contained within the syringe barrel without using airtight seals. A double walled stem cooperates with the barrel to form a rear tortuous path. A needle and hub assembly cooperates with a front bore in the barrel together with an overlying needle sheath and front cap to form a front tortuous path. The front and rear tortuous paths are maintained by a breakable bond between the cap and the stem until the syringe is to be used. Another embodiment includes a pin on the front cap which cooperates with the front barrel bore in place of the needle and hub assembly.

11 Claims, 5 Drawing Figures

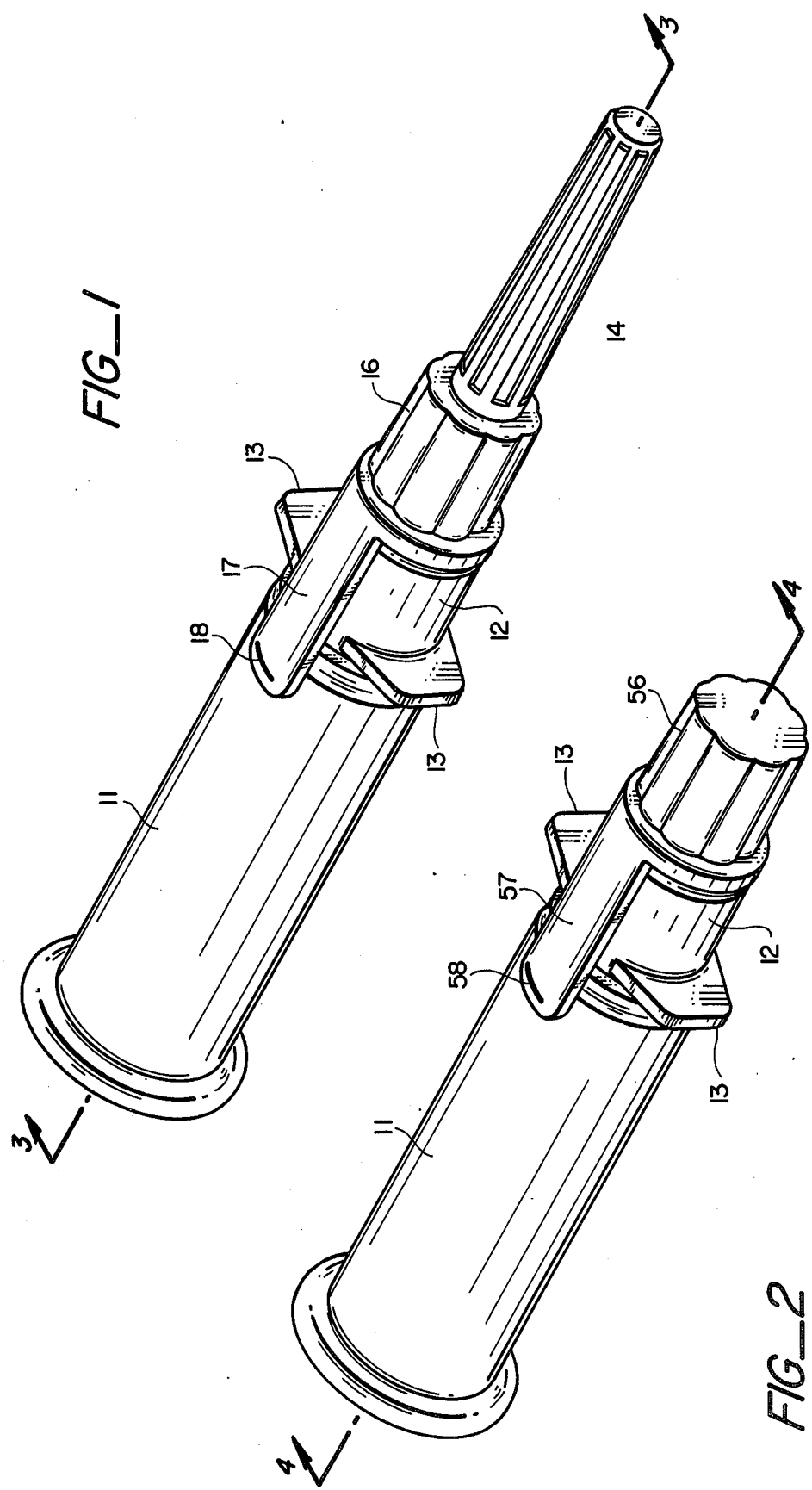

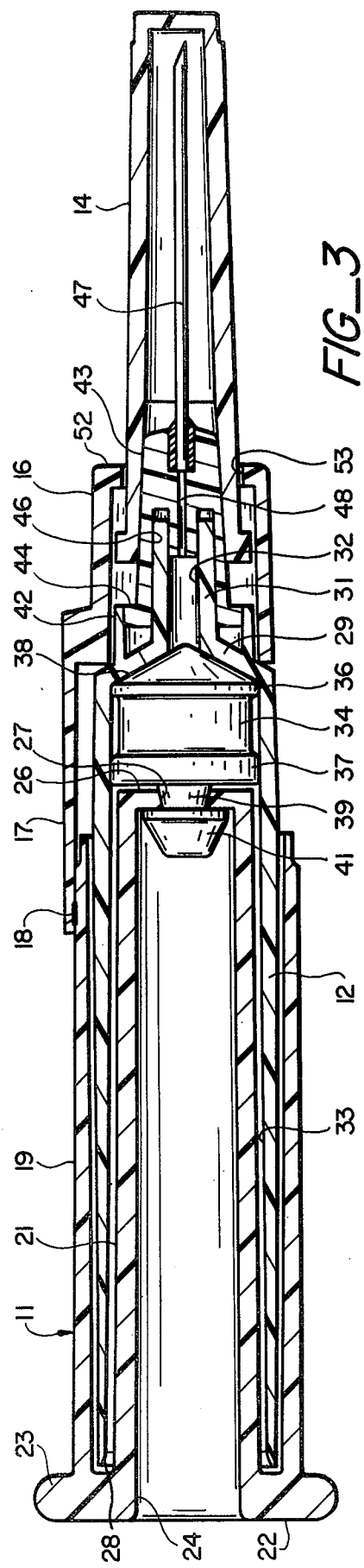
FIG_3
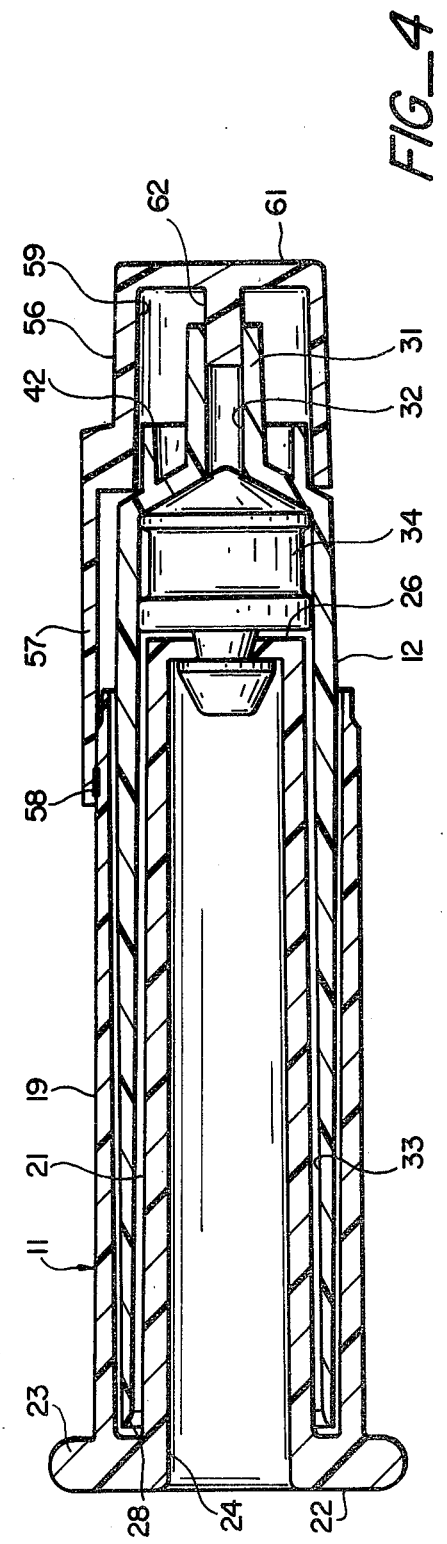
FIG_4

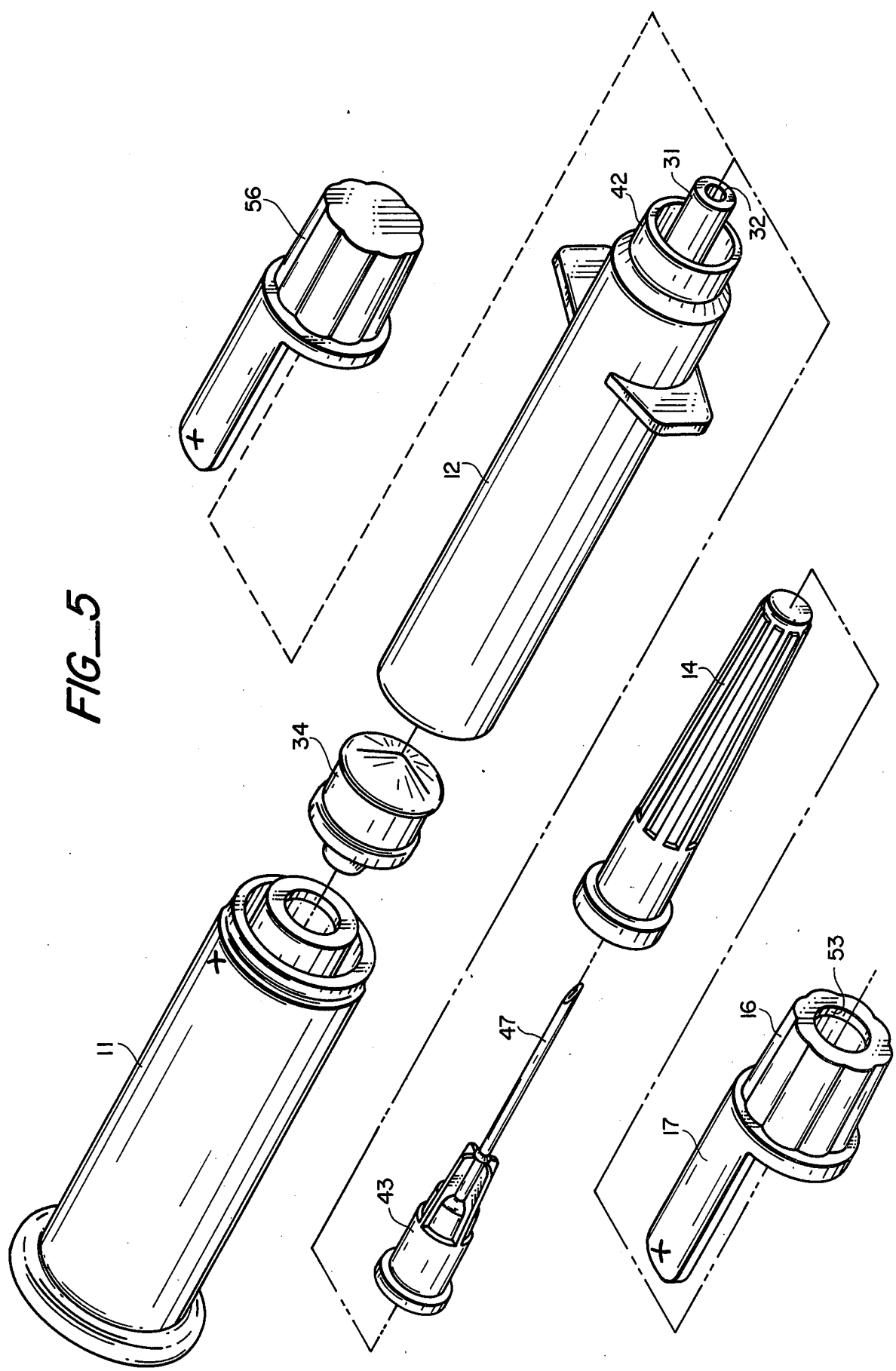

SELF-SEALED HYPODERMIC SYRINGE

BACKGROUND OF THE INVENTION

This invention relates to a disposable hypodermic syringe, and more particularly to such a syringe which is maintained in a sterile condition without external packaging.

Louis Pasteur in his experiments relative to the behavior of bacteria fashioned glass flasks with various neck shapes. Each flask contained an enclosed sterial media. The necks on some flasks allowed airborne dust particles to fall on the contained media, which soon became contaminated as evidenced by the appearance of bacterial growth. The media in those flasks with S-curved necks, or which presented a "tortuous path" for airborne dust and bacteria, remained sterile. The dust and bacteria were stopped at the openings to the curved necks, as well as at the curves in the necks. Hypodermic injection devices using Pasteur's "tortuous path" principle have long been known, as may be seen by the "Monoject" brochure, copyright 1973, by Sherwood Medical Industries, Inc.

A sterilized hypodermic syringe assembly is seen in U.S. Pat. No. 2,860,635 to E. H. Wilburn which includes a double walled piston assembly. The piston has an externally threaded head end upon which a piston plug is screwed. Simple molding processes are precluded by thread formations. A needle cap is provided to cover the front end and the needle extending therefrom. The needle cap is press fitted onto the front of the Wilburn assembly. Conceivably, unless protected by external packaging, handling could cause Wilburn's double walled piston assembly to withdraw wholly or partially from the barrel, or the protective needle cap to loosen from the interference fit and fall off exposing the needle.

U.S. Pat. No. 3,485,239 discloses a sterile syringe utilizing two strips of removable gas permeable tape to hold a needle covering cap in place, and to retain a plunger within the syringe barrel. The tape performs a sieving effect, resisting the package of pathogenic organisms toward the interior of the syringe after sterilization.

A self-sealed hypodermic syringe is needed which will maintain sterility without airtight seals, and which is firmly held in the sterile configuration by means of a single breakable bond until ready for use.

SUMMARY AND OBJECTS OF THE INVENTION

In general, the self-sealed hypodermic syringe includes a barrel which defines a medicament chamber therein, and which has an opening at both a front and rear end. Means mounted on the front end of the barrel provide a front tortuous path between the surrounding environment and the medicament chamber. A plunger assembly is mounted on the rear end of the barrel, movable between a telescoped forward position and a withdrawn rearward position. The plunger assembly forms, with the barrel, a rearward tortuous path between the surrounding environment and the medicament chamber when it is in the telescoped forward position. A tab is attached to the front means forming a tortuous path, which extends rearwardly to overlie a part of the plunger assembly. A breakable bond is formed between the tab and the plunger assembly in the telescoped forward position, and the medicament chamber is isolated from pathogenic organisms present in the surrounding environment.

It is an object of the present invention to provide a self-sealed hypodermic syringe which is maintained in a sterile condition without external packaging.

Another object of the present invention is to provide a self-sealed hypodermic syringe having cooperating parts which are easily manufactured and assembled, and therefore inexpensive.

Another object of the present invention is to provide a self-sealed hypodermic syringe which may or may not be provided with a protected hypodermic needle and hub assembly.

Another object of the present invention is to provide a self-sealed hypodermic syringe utilizing an elastic piston fabricated and assembled by the simplest processes.

Another object of the present invention is to provide a self-sealed hypodermic syringe having a combination seal and tamper-proof indicator.

Additional objects and features of the invention will appear from the following description in which the preferred embodiments have been set forth in detail in conjunction with the accompanying drawings.

BRIEF DESCRIPTION OF THE DRAWINGS

FIG. 1 is an isometric view of one embodiment of the present invention.

FIG. 2 is an isometric view of another embodiment of the present invention.

FIG. 3 is a sectional side view of the embodiment of FIG. 1.

FIG. 4 is a sectional view of the embodiment of FIG. 2.

FIG. 5 is an exploded view showing both the embodiments of FIGS. 1 and 2.

DESCRIPTION OF THE PREFERRED EMBODIMENTS

FIG. 1 shows the invention in perspective view having a rear mounted plunger assembly 11 overlying and slidable on a barrel 12. Plunger assembly 11 is shown in a depressed or "telescoped" position on barrel 12. A pair of laterally extending finger wings 13 are formed on barrel 12. Finger wings 13 are located just forward of the end of plunger assembly 11 when plunger assembly 11 is in the fully depressed or telescoped position. Plunger assembly 11 encloses a rear opening in barrel 12. A front opening in barrel 12 is closed by structure including a needle sheath 14, a front cap 16, and a tab 17 extending rearwardly from front cap 16. A breakable bond 18 is formed between cap 17 and the outer surface of plunger assembly 11, thereby retaining plunger assembly 11 in the telescoped position and retaining front cap 16 firmly in place. While unbroken, bond 18 provides a tamper-proof indication.

Greater detail of the embodiment of FIG. 1 may be seen by reference to FIG. 3. Plunger assembly 11 is seen to have an outer wall 19 and an inner wall 21 defining an annular space therebetween. The annular space between outer and inner walls 19 and 21 respectively is closed at the rear end thereof by a rear wall 22. Rear wall 22 also provides a bead 23 around the rear end of plunger assembly 11 which serves as means for grasping plunger assembly 11 to withdraw it from the telescoped position as shown in FIGS. 1 and 3 to a rearwardly extended position. Rear wall 22 may be seen to have a centrally disposed hole 24 therethrough aligned with the inner surface of inner wall 21. A forward wall 26 is formed across the front portion of inner wall 21 having an aperture 27 therethrough. It may therefore be seen that the portion of plunger assembly 11 described thus far including inner and outer walls 21 and 19 respectively, rear wall 22, front wall 26, and respective apertures 24 and 27, may be formed in a "one shot" injection molding process, eliminating the need for molds having expensive sliding cores or thread forming features.

Barrel 12 has a wall formed to fit within the annular space formed between inner and outer walls 21 and 19 on plunger assembly 11. Barrel 12 further has an open rearward end 28 through which inner wall 21 and front wall 26 on plunger assembly 11 extends. Barrel 12 also has a front wall 29 having a boss 31 extending forward therefrom with a bore 32 therethrough. A chamber 33 is formed bounded by the inner surfaces of the walls of barrel 12 and extending between open rearward end 28 and forward wall 29. Chamber 33 functions to receive medicaments to be injected by the hypodermic syringe.

An elastic piston 34 is formed to fit within chamber 33 for slidable motion along the length of chamber 33, having a forward land 36 and a rear land 37 compressed by and in engagement with the walls of chamber 33. A forward conical surface 38 on piston 34 is formed to substantially conform to the shape of the inner surface of wall 29 so that chamber 33 is substantially filled by inner wall 21, or the stem portion of plunger assembly 11 and piston 34, and is thereby completely emptied of contained medicaments when plunger assembly 11 is in the forward or telescoped position. Piston 34 also has a rearwardly extending protrusion consisting of a neck portion 39 and an enlarged end 41. Neck portion 39 is of a size to fit through aperture 27 and to be engaged by the walls defining aperture 27. Piston 34 is assembled in plunger assembly 11 by deforming enlarged end 41, and forcing it through aperture 27 until it resumes its normal shape against the back side of front wall 26. In this fashion piston 34 is mounted on forward wall 26 of plunger assembly 11, so that it may move along the length of chamber 33 in accordance with motion imparted to plunger assembly 11.

Barrel 12 has a forwardly extending skirt 42 spaced from boss 31, thereby forming an annular groove therebetween. A needle hub 43 has a flange 44 thereon which is formed to be engaged by the inner surface of skirt 42. Needle hub 43 also has a bore 46 therein which is formed to accept boss 31. A hollow needle 47, suitable for subcutaneous instrusion, is mounted in needle hub 43 being in communication with chamber 33 through bore 32 and a channel 48 in needle hub 43 aligned therewith.

Needle sheath 14 surrounds and encloses needle 47, engaging the outer surface of needle hub 43. Needle sheath 14 is frictionally engaged by the outer surface of needle hub 43. Front cap 16 has an inside dimension formed to accept and engage the outer surface of skirt 42. Front cap 16 has a front wall 52 having an aperture 53 therein, which is formed to surround that part of needle sheath 14 which overlies needle hub 43. Tab 17 extends rearwardly from front cap 16 to overlie outer wall 19 when plunger assembly 11 is in the forward or telescoped position. Breakable bond 18 is formed at the contacting surfaces between outer wall 19 and rearwardly extending tab 17.

It may be seen that a rear tortuous path between the external environment and chamber 33 exists along the interfaces between the inner surface of outer wall 19 and the outer surface of barrel 12, the closed rearward end of the annular space between outer and inner walls 19 and 21 and the end of barrel 12, and the inner surface of barrel 12 and the outer surface of inner wall 21. A front tortuous path is formed between the external environment and chamber 33 extending along the interface between front cap 16 and skirt 42, needle hub 43 and boss 31, and bore 32. A parallel front tortuous path is formed extending along the interfaces between needle sheath 14 and the walls defining aperture 53, needle sheath 14 and needle hub 43, and through hollow needle 47, channel 48, and bore 32. Medicament chamber 33 is therefore isolated from the surrounding environment by the aforementioned rear and front tortuous paths, whereby pathogenic organisms are excluded from medicament chamber 33.

Turning to FIG. 5, the manner in which the embodiment just described is assembled will be described. The double walled plunger assembly 11, as mentioned above, has a shape which allows a single step injection molding process to be used in manufacture. Piston 34 is also formed by a simple single step molding process using an elastic material. Barrel 12 is a simple shape formed by an injection molding process without using sliding cores or other expensive mold features. Needle hub 43 and needle 47 are formed as a unit through a simple molding process, wherein the needle 47 is molded in place in needle hub 43. Needle hub 43 snugly fits over boss 31 on barrel 12. Needle sheath 14 is a single step injection molded plastic part, snapping over the forward end of needle hub 43. Front cap 16 fits snugly over skirt 42 with needle sheath 14 extending through aperture 53. Tab 17 is shown extending rearwardly from front cap 16. It may be seen that the hypodermic syringe of FIG. 1 may be assembled in a matter of seconds from the inexpensively formed parts shown in exploded view in FIG. 5. Plunger assembly 11 is maintained in the depressed telescoped position by means of the bond 18, such as a heat bond, established between barrel 11 and tab 17 approximately at the positions marked X in FIG. 5.

The embodiment of FIG. 2 includes the rear mounted plunger assembly 11 described above for the embodiment of FIG. 1, the barrel 12 with laterally extending finger wings 13 thereon, and structure enclosing the front end of the hyperdomic syringe including a front cap 56. A rearwardly extending tab 57 is attached to front cap 56 to overlie a portion of the outer wall 19 on plunger assembly 11. A bond 58 is formed between the facing surfaces of outer wall 19 and tab 57.

FIG. 4 shows the embodiment of FIG. 2 including the structural details for plunger assembly 11 recited in the description of FIG. 3 above. The double walled plunger assembly 11 is inserted through the open end 28 of barrel 12 to serve as a "stem," and to provide the above described rear tortuous path between the external environment and chamber 33 within barrel 12. Piston 34 is formed as described above, of an elastic material to fit within chamber 33 for slidable motion along the length thereof. Piston 34 is mounted in front wall 26 extending across inner wall 21, so that motion of piston 34 along the length of chamber 33 is controlled by manipulation of plunger assembly 11 between a forward "telescoped" position and a rearward extended position. Front cap 56 has an inside diameter 59 which snugly fits about skirt 42. Front cap 56 has a front cap wall 61 on which is formed a rearwardly extending internal pin 62. Pin 62 is formed to be snugly received in bore 32 through boss 31. Consequently, a front tortuous path is provided between the external environment and medicament chamber 33 extending along the interfaces between front cap inside diameter 59 and skirt 42, and pin 62 and front bore 32. When the front cap 56 in FIG. 4 is positioned as shown, bond 58 is formed between facing surfaces on outer wall 19 and rearwardly extending tab 57 where tab 57 overlies plunger assembly 11.

FIG. 5 serves to show an exploded view of the assembly of the embodiment of FIGS. 2 and 4 utilizing the same plunger assembly 11, piston 34 and barrel 12 as are utilized in the embodiment of FIGS. 1 and 3. Front cap 56 is shown to be installed overlying skirt 42, so that pin 61 engages the bore 32 in boss 31. With front cap 56 installed, and plunger assembly 11 in the forwardmost telescoped position, tab 57 is bonded to that portion of outer wall 19 on plunger assembly 11 which it overlies. In this fashion the rear and front tortuous paths are maintained and the syringe is shown to be free of tampering, until the bond, indicated as positioned approximately at X, is broken just prior to use of the hypodermic syringe.

A hypodermic syringe has been disclosed which may or may not contain a needle hub and hollow needle assembly, and which is maintained in a telescoped condition by a breakable bond until ready for use. The bond also provides indication of tampering when broken. While in the telescoped condition, the hypodermic syringe isolates the medicament chamber surfaces from the external environment by providing rear and front tortuous paths therebetween, which are known to bar the migration of pathogenic organisms. Moreover, the embodiments of the hypodermic syringe disclosed herein maintain such isolation of the medicament chamber without external package requirements and without the necessity for airtight seals between mating parts.

What is claimed is:

1. A self-sealed hypodermic syringe, comprising
    an inner barrel having a rear open end,
    a front wall in said inner barrel, whereby a chamber is defined between said front wall and said rear open end within said inner barrel,
    a boss extending from said front wall having a bore therethrough in communication with said chamber,
    a skirt extending from said inner barrel concentric with and spaced from said boss, whereby an annular groove is formed therebetween,
    means for closing said bore formed to fit over said skirt,
    a unitary double walled stem member having an inner wall and an outer wall spaced therefrom, thereby forming an annular space therebetween having a rear closed end and a front open end,
    said annular space being formed to accept said inner barrel, whereby said stem member is movable between a telescoped position with said front open end proximate to said front wall and an extended position remote therefrom, and a rear tortuous path between the surrounding environment and said chamber is formed extending along the interfaces between said outer wall and said inner barrel outside surface, said rear closed end of said annular space and said rear open end of said inner barrel, and said inner wall and said inner barrel inner surface,
    a front stem member wall adjacent to said front open end having a hole therethrough,
    a resilient plunger formed for sliding motion within said inner barrel between said front wall and said rear open end,
    a protrusion on said resilient plunger having an enlarged end and a neck portion substantially of the same dimensions as said hole, so that when said enlarged end is deformed and forced through said hole with said neck portion engaged therein, said resilient plunger is retained in said front stem wall,
    a tab on said means for closing said bore extending rearwardly to overlie said outer wall when said stem member is in said telescoped position,
    and a breakable bond between said tab and said outer wall, whereby said bore is maintained closed and said stem member is maintained in said telescoped position isolating said chamber from the surrounding environment until said bond is broken prior to use.

2. A self-sealed hypodermic syringe as in claim 1 wherein said means for closing said bore comprises
    a front cap having a closed front end,
    an internal pin on said closed front end extending rearwardly therefrom,
    said internal pin being formed to fit in said bore, whereby a tortuous front path between the surrounding environment and said chamber is formed extending along the interfaces between said front cap and said skirt, and said pin and said bore.

3. A self-sealed hypodermic syringe as in claim 1 wherein said means for closing said bore comprises
    a needle hub formed to fit over said boss,
    a needle extending through said hub in communication with said bore, and having a forwardly protruding segment,
    a needle sheath enclosing said forwardly protruding segment of said needle and engaging the outer surface of said needle hub,
    a front cap snugly engaging the outer surface of said skirt,
    and a front end on said front cap having a hole therethrough formed to snugly engage said needle sheath, said tab being attached to said front cap, whereby a tortuous path between the surrounding environment and said chamber is formed extending along the interfaces between said front cap and said skirt, said needle hub and said boss, and said bore.

4. A self-sealed hypodermic syringe, comprising
    a syringe barrel having side walls defining a medicament chamber therein and having a rear open end,
    a front wall in the other end of said syringe barrel,
    a boss on said front wall extending forwardly therefrom and having a bore therethrough in communication with said medicament chamber,
    a skirt on said syringe barrel surrounding said boss,
    a plunger cooperating with said syringe barrel side walls and said rear open end forming a tortuous rear path between the external environment and said medicament chamber,
    means cooperating with said skirt, boss and bore forming a front tortuous path between the external environment and said medicament chamber,
    and a tab extending from said last named means rearwardly to said plunger and forming a breakable bond therebetween, whereby said plunger is retained in fixed position and said tortuous front and rear paths are maintained until said bond is broken.

5. A self-sealed hypodermic syringe as in claim 4 wherein said plunger comprises a double walled cylinder having an outer wall overlying said syringe barrel and an inner wall extending into said medicament chamber adjacent to said side walls, a front plunger wall across the front end of said inner wall having an aperture therethrough, a resilient piston formed to slidably fit within said medicament chamber, a protrusion formed integrally with and extending from the rear side of said resilient piston, a neck on said protrusion having dimensions substantially the same as said aperture, and an enlarged end on said protrusion, so that when said enlarged end is deformed and forced through said aperture said neck is snugly engaged therein.

6. A self-sealed hypodermic syringe as in claim 4 wherein said means cooperating with said skirt, boss, and bore comprises a cap overlying said skirt, a closed front wall on said cap, and an internal pin on said closed front wall extending rearwardly and formed to snugly fith within said bore.

7. A self-sealed hypodermic syringe as in claim 4 wherein said means cooperating with said skirt, boss and bore comprises a needle hub formed to fit over said boss, a hollow needle extending through said hub in communication with said bore, and having a portion protruding forwardly therefrom, a needle sheath enclosing said portion protruding forwardly and engaging the outer surface of said needle hub, a front cap snugly engaging the outer surface of said skirt, and a front end on said front cap having a hole therethrough formed to snugly engage said needle sheath.

8. A self-sealed hypodermic syringe comprising a barrel defining a medicament chamber therein and having an opening at both a front and a rear end thereon, means for forming with said barrel a front tortuous path between the surrounding environment and said medicament chamber mounted on said barrel front end, a plunger assembly mounted on said barrel rear end movable between a telescoped forward position and a withdrawn rearward position, said plunger assembly forming with said barrel a rear tortuous path between the surrounding environment and said medicament chamber when in said telescoped forward position, a tab attached to said means for forming a front tortuous path extending rearwardly to overlie a portion of said plunger assembly, and a breakable bond between said tab and said plunger assembly in said telescoped forward position, whereby said front and rear tortuous paths are maintained while said breakable bond is unbroken.

9. A self-sealing hypodermic syringe as in claim 8 wherein said means for forming a front tortuous path comprises a cap snugly engaging an outer surface on said barrel and enclosing the front end thereof, and an internal pin in said cap formed to fit within said front end opening.

10. A self-sealing hypodermic syringe as in claim 8 wherein said means for forming a front tortuous path comprises a needle hub attached to said barrel front end, a hollow needle mounted in said needle hub extending therethrough in communication with said front end opening and having a forward extending portion, a needle sheath enclosing said forward extending portion and engaging said needle hub, a cap snugly engaging an outer surface on said barrel at said front end, and a front wall on said cap having a hole therethrough formed to snugly engage said needle sheath.

11. A self-sealing hypodermic syringe as in claim 8 wherein said plunger assembly comprises a stem having an outer wall and an inner wall forming an annular space therebetween having a closed rear end and an open front end formed to accept said barrel rear end, a front stem wall extending across the front end of said inner wall having a hole therethrough, an elastic piston formed to tightly fit within said barrel disposed for sliding motion along the length of said medicament chamber, and a protrusion extending from the back of said piston having a neck of substantially the same dimensions as said hole and an enlarged end, whereby said enlarged end is deformed when forced through said hole and said elastic piston is sealably retained in said front stem wall.

* * * * *